United States Patent
Kim et al.

(10) Patent No.: US 9,901,370 B2
(45) Date of Patent: Feb. 27, 2018

(54) TUBE INSERTION DEVICE HAVING END EFFECTOR CAPABLE OF CHANGING DIRECTION

(71) Applicant: KOREA INSTITUTE OF SCIENCE AND TECHNOLOGY, Seoul (KR)

(72) Inventors: Keri Kim, Seoul (KR); Sung Chul Kang, Seoul (KR); Soojun Lee, Seoul (KR); Woosub Lee, Seoul (KR); Sangmyung Kim, Seoul (KR); Suhyeon Gim, Yongin-si (KR)

(73) Assignee: Korea Institute of Science and Technology, Seoul (KR)

( * ) Notice: Subject to any disclaimer, the term of this patent is extended or adjusted under 35 U.S.C. 154(b) by 1159 days.

(21) Appl. No.: 14/043,911

(22) Filed: Oct. 2, 2013

(65) Prior Publication Data
US 2015/0032117 A1    Jan. 29, 2015

(30) Foreign Application Priority Data
Jul. 29, 2013    (KR) ........................ 10-2013-0089474

(51) Int. Cl.
*A61B 17/34*    (2006.01)
*A61B 90/00*    (2016.01)
(Continued)

(52) U.S. Cl.
CPC ...... *A61B 17/3415* (2013.01); *A61B 17/3417* (2013.01); *A61B 17/3421* (2013.01);
(Continued)

(58) Field of Classification Search
CPC ............ A61B 17/3415; A61B 17/3417; A61B 2034/301; A61B 1/00098;
(Continued)

(56) References Cited

U.S. PATENT DOCUMENTS

| 5,810,880 A * | 9/1998 | Jensen | A61B 34/76 |
| | | | 403/316 |
| 2006/0074383 A1* | 4/2006 | Boulais | A61B 1/0052 |
| | | | 604/95.04 |

(Continued)

FOREIGN PATENT DOCUMENTS

| KR | 10-0990992 B1 | 10/2010 |
| KR | 10-1155464 B1 | 6/2012 |
| KR | 10-1258779 B1 | 4/2013 |

OTHER PUBLICATIONS

Yamashita, H., et al. "Miniature bending manipulator for fetoscopic intrauterine laser therapy to treat twin-to-twin transfusion syndrome." Surgical endoscopy 22.2 (2008): 430-435.

*Primary Examiner* — Bradley Osinski
(74) *Attorney, Agent, or Firm* — NSIP Law

(57) ABSTRACT

A tube insertion device which inserts a tube into a line path to perform an operation has an elongated hollow tube, an end effector connected to a front end of the tube such that the direction of the end effector is changed with respect to the tube, a plurality of wires connected to the end effector and extended into the tube and a tension controller controlling tensions of the plurality of wires. The tension controller controls tensions of a pair of wires facing each other in the opposite directions, in order to change the direction of the end effector.

11 Claims, 10 Drawing Sheets

(51) Int. Cl.
  *A61B 17/00* (2006.01)
  *A61B 17/29* (2006.01)
  *A61B 1/00* (2006.01)
  *A61B 34/30* (2016.01)

(52) U.S. Cl.
  CPC ........ *A61B 17/3478* (2013.01); *A61B 90/361* (2016.02); *A61B 1/00098* (2013.01); *A61B 2017/003* (2013.01); *A61B 2017/00331* (2013.01); *A61B 2017/00398* (2013.01); *A61B 2017/00809* (2013.01); *A61B 2017/2927* (2013.01); *A61B 2034/301* (2016.02)

(58) Field of Classification Search
  CPC .. A61B 2017/2927; A61B 2017/00331; A61B 2017/003
  See application file for complete search history.

(56) References Cited

U.S. PATENT DOCUMENTS

| | | | |
|---|---|---|---|
| 2008/0027285 A1* | 1/2008 | Yasunaga | A61B 1/0058 600/150 |
| 2009/0143647 A1 | 6/2009 | Banju | |
| 2012/0089154 A1 | 4/2012 | Green et al. | |
| 2013/0018303 A1 | 1/2013 | Webster et al. | |

\* cited by examiner

TUBE INSERTION DEVICE HAVING END EFFECTOR CAPABLE OF CHANGING DIRECTION

CROSS-REFERENCE TO RELATED APPLICATION

This application claims priority to Korean Patent Application No. 10-2013-0089474, filed on Jul. 29, 2013, and all the benefits accruing therefrom under 35 U.S.C. § 119, the contents of which in its entirety are herein incorporated by reference.

BACKGROUND

1. Field

Exemplary embodiments relate to a tube insertion device, and more particularly, to a tube insertion device capable of inserting a long hollow tube into a long line path so as to perform a predetermined operation.

2. Description of the Related Art

Representative examples of a tube insertion device capable of inserting a long and hollow tube into a narrow space to perform a predetermined operation may include a micro-surgery instrument for a minimally invasive surgery.

The minimally invasive surgery refers to a surgery for minimizing an incision without opening the abdomen. When the minimally invasive surgery is applied, an incision is so small that a scar or aftereffect may be minimized and a patient may be quickly recovered.

Much research has been conducted on a method for controlling micro-surgery instruments for the minimally invasive surgery, because a predetermined operation such as a surgery must be performed within a narrow space.

FIG. 1 illustrates an active cannular as a conventional micro-surgery instrument, which has been disclosed in US Patent Laid-open Publication No. 2013/0018303.

Referring to FIG. 1, the active cannular is made of a superelastic shape-memory alloy having a curvature, and includes a plurality of overlapping flexible tubes which have different diameters and curvatures. The position of an end effector 125 may be changed according to an input angle based on an interaction between the tubes. When three tubes 110, 115, and 120 are used, the tubes 110, 115, and 120 may have a diameter of 2 mm to 5 mm and a length of 10 cm to 20 cm.

According to the related art, an energy formula is used to estimate an angle at which the energy of the overlapping tubes 110, 115, and 120 is minimized and a final position of the end effector 125.

The three tubes 110, 115, and 120 are divided into an outer flexible tube 110, a middle flexible tube 115, and an inner flexible tube 120, which independently have rotational degrees of freedoms and translational degrees of freedoms. That is, the outer flexible tube 110 has an outer rotational degree of freedom 305 and an outer translational degree of freedom 310, the middle flexible tube 115 has a middle rotational degree of freedom 315 and a middle translational degree of freedom 320, and the inner flexible tube 120 has an inner rotational degree of freedom 325 and an inner translational degree of freedom 330.

Referring to FIG. 1, as the three tubes 110, 115, and 120 are properly rotated and/or translationally moved, the three tubes 110, 115, and 120 may be properly bent to correspond to the shape of a space into which an instrument is to be inserted. Then, the end effector 125 may be located at a desired position.

According to the related art, the end effector 125 may be located at a desired position, but the orientation of the end effector 125 cannot be locally changed at the corresponding position. Thus, the end effector 125 has a limitation in operation.

In general, since the end effector 125 used in the minimally invasive surgery has a very small size, it is very difficult to directly mount a motor for direction change on the end effector 125.

SUMMARY

In accordance with an aspect of the present disclosure, there may be provided a tube insertion device having a direction adjustment unit capable of effectively controlling the direction of an ultra-small end effector connected to a front end of a micro tube.

A tube insertion device which inserts a tube into a line path to perform an operation includes: an elongated hollow tube; an end effector connected to a front end of the tube such that the direction of the end effector is changed with respect to the tube; a plurality of wires connected to the end effector and extended into the tube; and a tension controller controlling tensions of the plurality of wires. The tension controller controls tensions of a pair of wires facing each other in the opposite directions, in order to change the direction of the end effector.

The tension controller may include: an elastic body connected to a first wire of the pair of wires and providing a tension to the first wire through an elastic force to pull the first wire toward a rear end of the tube; and a moving body connected to a second wire of the pair of wires, and moved to approach or separate from the tube, thereby controlling a tension of the second wire in the opposite direction of the tension of the first wire.

The tube insertion device may further include a fixing body fixing the rear end of the tube. The tension controller may be coupled to a rear end of the fixing body, and the longitudinal directions of the tube and the tension controller are aligned with each other.

The tube and the tension controller may be coupled to the fixing body so as to rotate around the longitudinal central axis of the tube, and the tube and the tension controller may be simultaneously rotated by a first motor provided in the fixing body.

The tube may include a flexible tube or a micro tube made of a superelastic shape-memory alloy having a predetermined curvature.

The end effector may be connected to the tube through a joint such that the direction of the end effector is changed upward and downward with respect to the tube, and the pair of wires may be disposed in a vertical direction so as to be connected to the end effector.

The end effector may include a micro operation device which photographs, incises, cuts, penetrates, sutures, connects, welds, or lights an operation target around an insertion position inside the line path or performs an operation of applying or injecting a medicine to the operation target.

The elastic body may include a coil-type spring, the first wire may pass through the center of the coil-type spring, and the first and second wires may be extended in parallel along the longitudinal direction of the tension controller inside the tension controller.

The tension controller may include: a frame rotatably coupled to the fixing body; and a second motor fixed to a rear end of the frame and coupled to the rear end of the moving body so as to linearly move the moving body forward or backward.

The frame may include a position sensor to sense the position of the moving body.

The fixing body may be moved forward or backward by the third motor so as to move the tube forward or backward.

DETAILED DESCRIPTION

Figure 1:
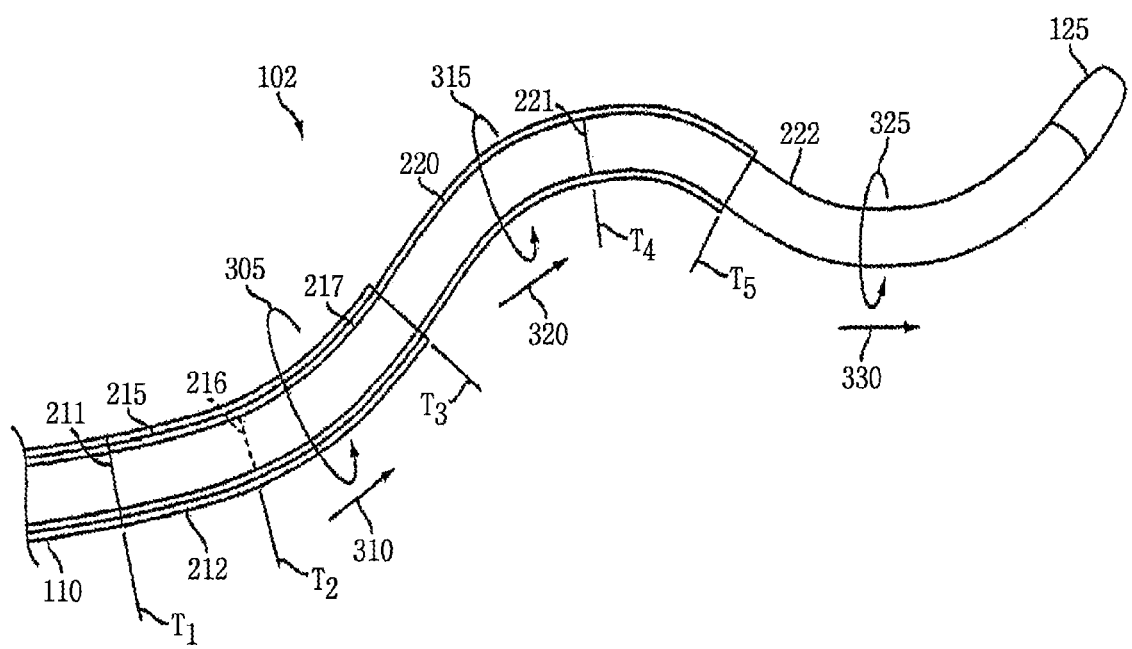
FIG. 1 illustrates a conventional tube assembly.

Exemplary embodiments of the present disclosure will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

Figure 2:
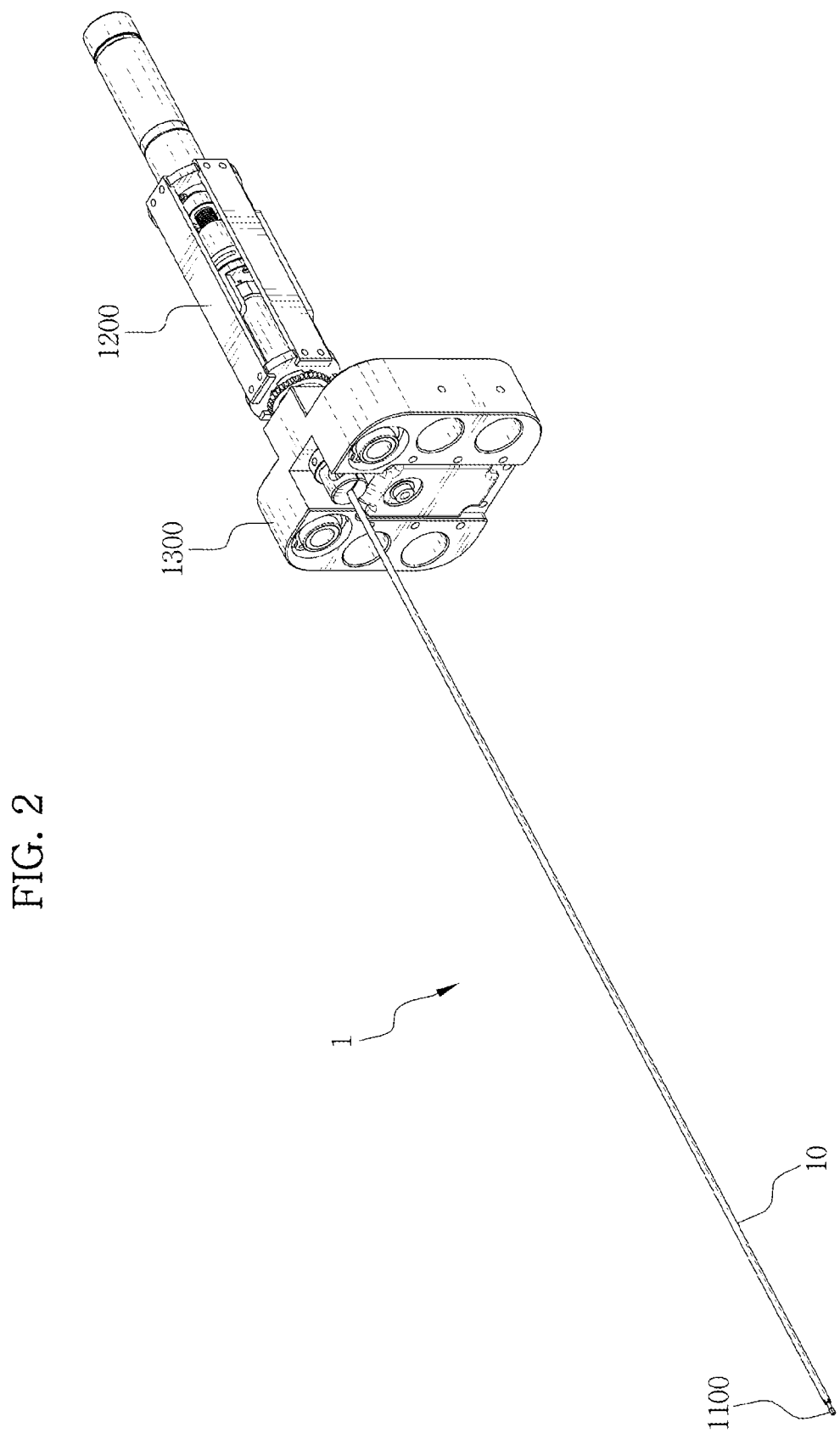
FIG. 2 is a perspective view of a tube insertion device according to an embodiment of the present disclosure.

FIG. 2 is a perspective view of a tube insertion device 1 according to an embodiment of the present disclosure.

Referring to FIG. 2, the tube insertion device 1 according to the embodiment includes an elongated hollow tube 10, an end effector 1100, a fixing body 1300, and a tension controller 1200. The end effector 1100 is connected to a front end of the tube 10 such that the direction of the end effector 1100 may be changed with respect to the tube 10. The fixing body 1300 serves to fix a rear end portion of the tube 10. The tension controller 1200 is coupled to a rear end of the fixing body 1300 and serves to change the direction of the end effector 1100.

Figure 3:
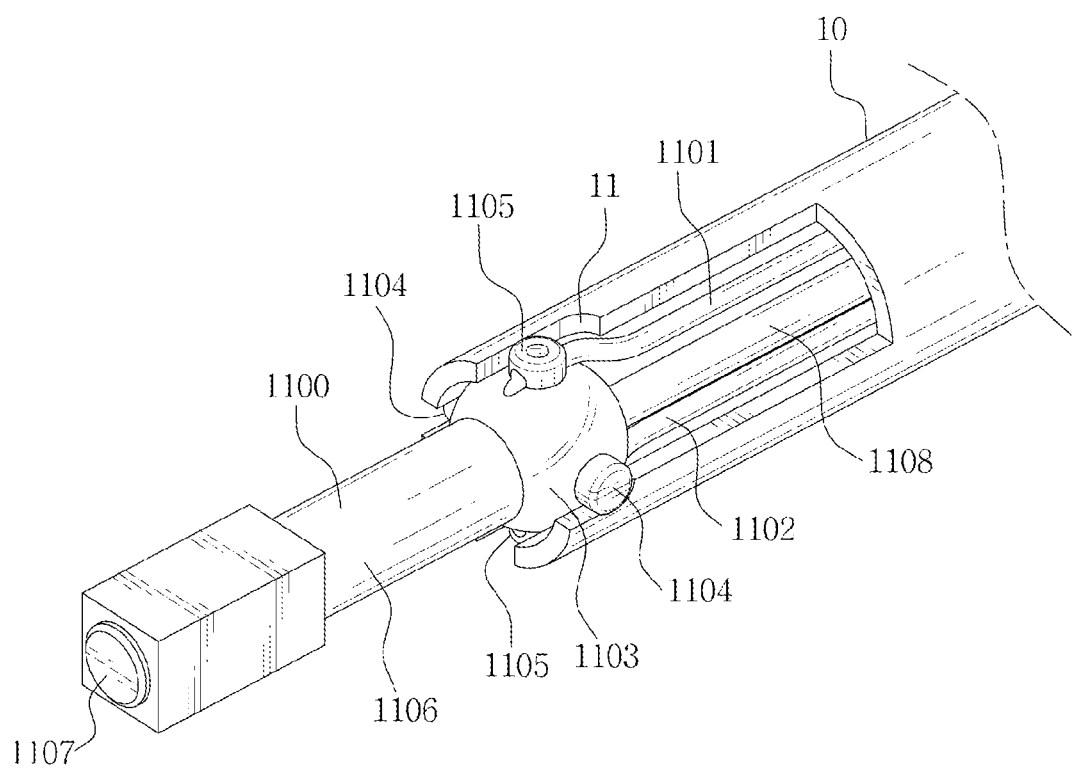
FIGS. 3 and 4 are expanded views of an end effector and a tube according to the embodiment.
Figure 4:
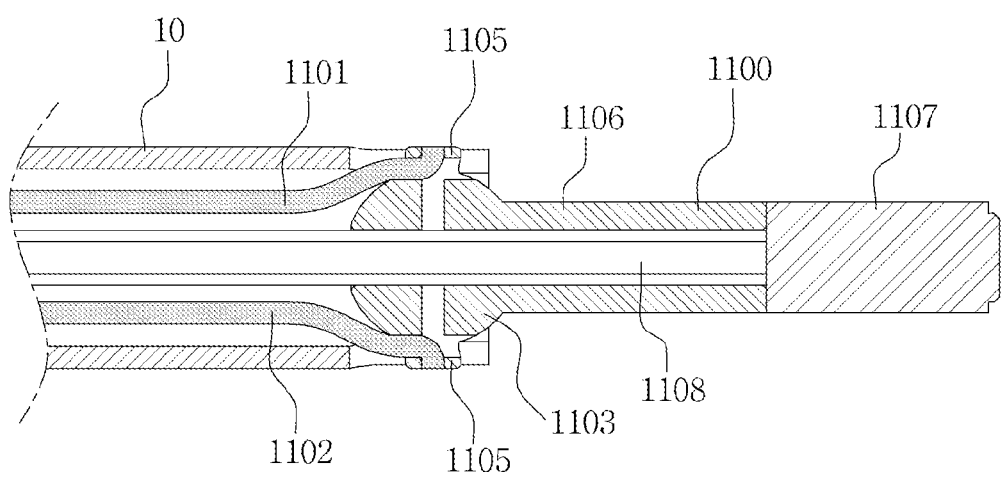

FIGS. 3 and 4 are expanded views of the end effector 1100 and the tube 10. For convenience of description, FIG. 3 illustrates a state in which the tube 10 is partially cut.

Referring to FIGS. 3 and 4, the tube insertion device 1 according to the embodiment includes a micro camera serving as the end effector 1100 which is inserted into a line path so as to take an image around an insertion position.

The end effector 1100 includes a body 1107, a connection 1106, and a spherical joint 1103. The body 1107 includes operation tools such as a lens and various electronic devices, which are embedded therein. The connection 1106 is connected to a rear end of the body 1107. The spherical joint 1103 is inserted into the tube 10.

The spherical joint 1103 has rotational joints 1104 formed in the left and right directions of the tube 10, such that the direction of the end effector 1100 may be changed upward and downward with respect to the tube 10.

The terms "upward and downward" and "left and right" are not used to limit the absolute directions of the end effector 1100 with respect to the ground, and relatively indicate two crossing directions perpendicular to each other.

The spherical joint 1103 has wire coupling portions 1105 formed at the top and bottom thereof. A pair of wires 1101 and 1102 arranged in a vertical direction are coupled to the wire coupling portions 1105, respectively, so as to face each other. Referring to FIG. 3, the tube 10 has holes 11 formed at the top and bottom of a front end thereof in the longitudinal direction thereof. Thus, when the direction of the end effector 1100 is changed, the tube 10 does not interfere with motions of the wire connection portions 1105.

Figure 5:
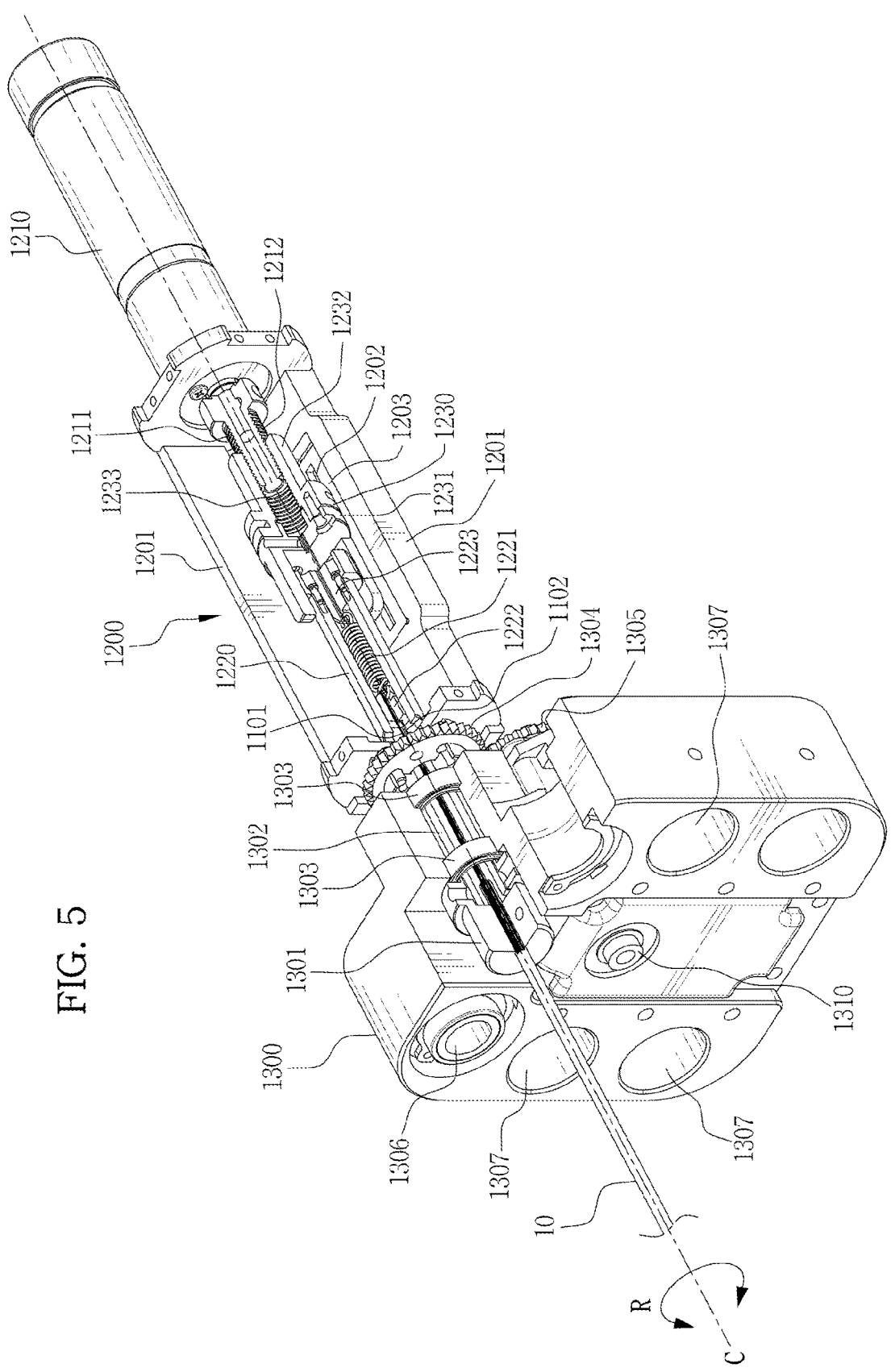
FIGS. 5 and 6 are front and rear perspective views of the tube insertion device in a state in which the end effector is omitted from the drawings.
Figure 6:
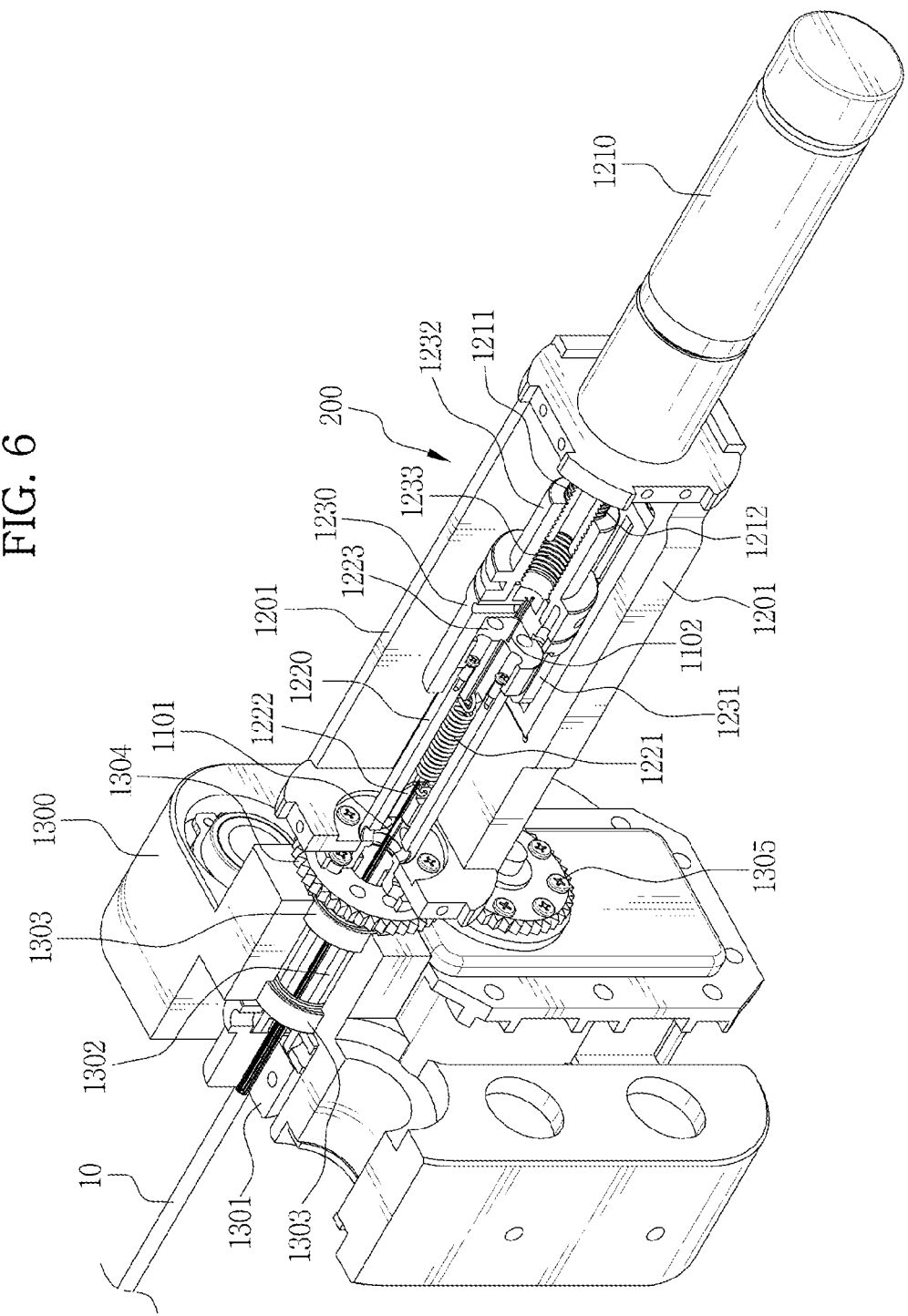

The pair of wires 1101 and 1102 are extended to the tension controller 1200 through the inside of the tube 10 (refer to FIGS. 5 and 6). A wire casing 1108 is formed at the rear end of the spherical joint 1103 of the end effector 1100. The wire casing 1108 serves to house a wire which is electrically connected to an electronic part inside the body 1107, supplies power to the corresponding part, and transmits and receives data. The wire casing 1108 is extended between the pair of wires 1101 and 1102 inside the tube 10.

The end effector 1100 is not limited to a camera, but may include an arbitrary micro-operation device capable of performing various operations in a line path. For example, the end effector 1100 may include an operation device capable of photographing, incising, cutting, penetrating, connecting (welding), or lighting an operation target around an insertion position or performing an operation of applying or injecting a medicine to the operation target. When the tube insertion device is used for a minimally invasive surgery, a small surgery instrument such as camera, surgery scalpel, scissor, injector or laser device may correspond to the end effector 1100.

At this time, the wire casing 1108 may serve as a path through which medicine or the like is supplied to the end effector 1100.

FIGS. 5 and 6 are front and rear perspective views of the tube insertion device 1 in a state in which the end effector 1100 is omitted from the drawings.

Referring to FIGS. 5 and 6, the fixing body 1300 fixes the rear end of the tube 10 through a clamp 1301. A cylindrical hollow shaft 1302 is fixed to a rear end of the clamp 1301, and a first gear 1304 is coupled to a rear end of the shaft 1302. The tension controller 1200 is fixed and coupled to the first gear 1304.

The tube 10, the shaft 1302, and the tension controller 1200 have a hollow portion formed therein, and are connected to each other such that the wires 1101 and 1102 pass through the tube 10, the shaft 1302, and the tension controller 1200. The longitudinal directions of the tube 10 and the tension controller 1200 are aligned with each other.

The shaft 1302 is rotatably connected to the fixing body 1300 through two bearings 1303, and the first gear 1304 is engaged with a second gear 1305 connected to a first motor 1310 provided in the fixing body 1300.

According to the above-described structure, the torque of the first motor 1310 rotates the first gear 1304 through the second gear 1305, and the first gear 1304 rotates the shaft 1302 with respect to the fixing body 1300. As the shaft 1302 is rotated, the tube 10 and the tension controller 1200 are simultaneously rotated with respect to the fixing body 1300. The rotations of the tube 10 and the tension controller 1200 are performed in a circumferential direction R of a longitudinal central axis C of the tube 10.

The tension controller 1200 includes a frame 1201, a tension control unit, and a second motor 1210. The frame 1201 is rotatably coupled to the fixing body 1300, the tension control unit is positioned inside the frame 1201, and connected to the wires 1101 and 1102 so as to control the tension. The second motor 1210 is fixed to a rear end of the frame 1201 so as to operate the tension control unit.

The tension control unit includes an elastic body case 1220, a moving body 1230, and a rotating connection 1211, which are sequentially positioned from the front side. The elastic body case 1220 serves to house the elastic body 1221 and has a front end fixed to the frame 1201. The moving body 1230 is positioned at a rear read of the elastic body case 1220 and linearly moves along a guide groove 1202 formed in the frame 1201. The rotating connection 1211 connects the moving body 1230 and the second motor 1210. The elastic body 1221 according to the embodiment may include a coil-type spring.

Figure 7:
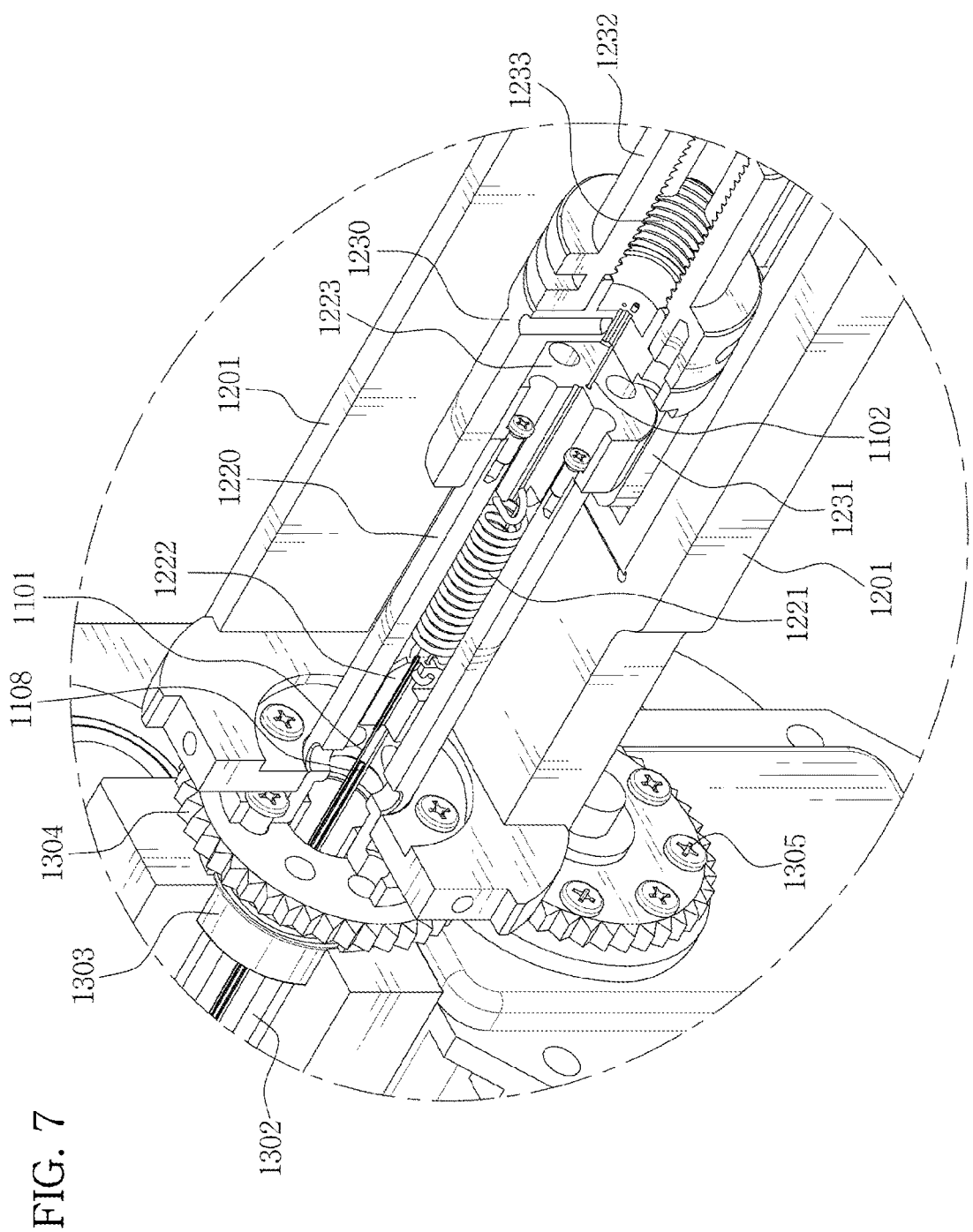
FIG. 7 is an expanded view of a part of FIG. 6.

As illustrated in FIG. 7, the elastic body case 1220 includes a body, a fixing hook 1223, and a moving hook 1222. The body is formed in a hollow cylinder type and houses the elastic body 1221 therein. The fixing hook 1223 is coupled to a rear end of the body so as to fix the rear end of the elastic body 1221. The moving hook 1222 may linearly move inside the body without rotation so as to fix the front end of the elastic body 1221.

The pair of wires 1101 and 1102 extended toward the rear end of the tube 10 and passing through the shaft 1302 of the fixing body 1300 are extended in parallel inside the tension controller 1200.

The first wire 1101 of the pair of wires 1101 and 1102 is fixed to the moving hook 1222. The second wire 1102 passes through the moving hook 1222 and connects to the moving body 1230 through the fixing hook 1223 via the center of the elastic body 1221. At this time, the moving hook 1222 and the fixing hook 1223 do not interfere with the motion of the second wire 1102.

The moving body 1230 may linearly move along the guide groove 1202 formed in the frame 1201 without rotation. Furthermore, the moving body 1230 includes a straight connection 1231 and a rotating connection 1232. The straight connection 1231 is connected to the second wire 1102, and the rotating connection 1232 is connected to the rear end of the straight connection 1231 and has a screw thread 1233 formed on the inner surface thereof.

The rotating connection 1232 is connected to the second motor 1210 and screwed to a rotating connection 1211 having a screw thread 1212 formed on the outer surface thereof. Thus, when the second motor 1210 is rotated, the moving body 1230 is moved forward or backward inside the frame 1201 through an interaction between the rotating connection 1232 and the rotating connection 1211.

Although not illustrated in detail, the frame 1201 includes a position sensor 1302 capable of sensing the position of the moving body 1230, in order to precisely control the forward or backward position of the moving body 1230.

According to the embodiment, the tension controller 1200 controls the tensions of the pair of wires 1101 and 1102 facing each other, in order to change the direction of the end effector 1100. Hereafter, referring to FIG. 8, the tension controller 1220 will be described in more detail.

The elastic body 1221 of the tension controller 1220 connected to the first wire 1101 maintains a state in which the elastic body 1221 is slightly extended even when the moving hook 1222 is moved backward to the maximum extent (right direction of FIG. 8), and thus provides an elastic force to pull the first wire 1101 toward the rear end of the tube 10 (right direction of FIG. 8) such that the first wire 1101 is stretched tight at all times. The moving body 1230 is linearly moved to approach or separate from the tube 10, thereby controlling the tension of the second wire 1102.

Figure 8:
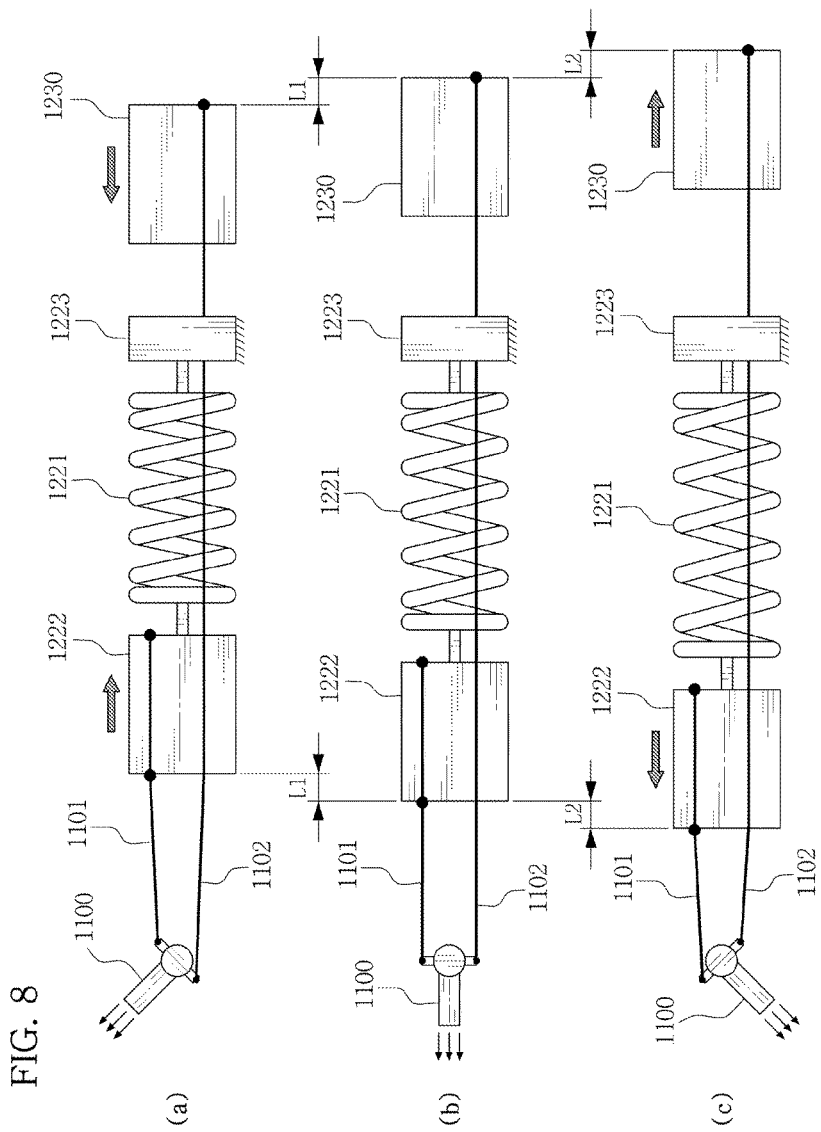
FIG. 8 is a diagram for explaining a process of changing the direction of the end effector of the tube insertion device according to the embodiment.

FIG. 8(*b*) illustrates the tension controller in a normal state.

In the normal state, the elastic force of the elastic body 1221 pulls the first wire 1101 in the right direction such that the tensions of the first and second wires 1101 and 1102 are balanced in a state in which the end effector 1100 faces the front side.

When the direction of the end effector 1100 is intended to be changed upward, the second motor 210 moves the moving body 1230 forward as illustrated in FIG. 8(*a*).

Thus, the tension applied to the second wire 1102 decreases more than the tension applied to the first wire 1101. The moving hook 1222 pulls the first wire 1101 in the right direction, while moved right by an elastic restoring force of the elastic body 221. Then, the end effector 1100 is included upward.

When the moving hook 1222 is moved by a moving distance L1 of the moving body 1230, the second wire 1102 is stretched tight to limit the movement of the moving hook 1222. As the tension applied to the first wire 1101 and the tension of the second wire 1102 are balanced again by the elastic force of the elastic body 1221, the end effector 1100 is fixed in a state in which it is inclined upward at a predetermined angle.

On the other hand, when the direction of the end effector 1100 is intended to be changed downward, the second motor 210 moves the moving body 1230 backward as illustrated in FIG. 8(*c*).

Thus, the tension applied the second wire 1102 increases, and the second wire 1102 pulls the end effector 1100 downward. Then, as the moving hook 1222 is moved left, the end effector 1100 is inclined downward.

When the moving body 1230 is stopped, the end effector 1100 maintains a state in which it is inclined downward by the tension of the second wire 1102. At this time, the moving hook 1222 is moved by a moving distance L2 of the moving body 1230, and the elastic force of the elastic body 1221 provides a force to pull the first wire 1101 in the right direction. Then, the first wire 1101 is stretched tight to balance the tensions of the first and second wires 1101 and 1102.

When the direction of the end effector 1100 is changed through the above-described structure, only the wires may be disposed in the tube 10, and the components for changing the direction of the end effector 1100 by controlling the tensions of the wires may be installed outside the tube 10. Thus, a micro tube having a very small diameter may be properly utilized as the tube 10.

Furthermore, since a flexible wire is used to change the direction of the end effector 1100, the tube 10 may be formed of a flexible tube.

In accordance with the embodiment of the present disclosure, the tube 10 may be made of a superelastic shape-memory alloy having a predetermined curvature, and may be inserted into another tube having a larger diameter than the tube 10 and a different curvature from the tube 10, thereby constituting an active cannular.

Figure 9:
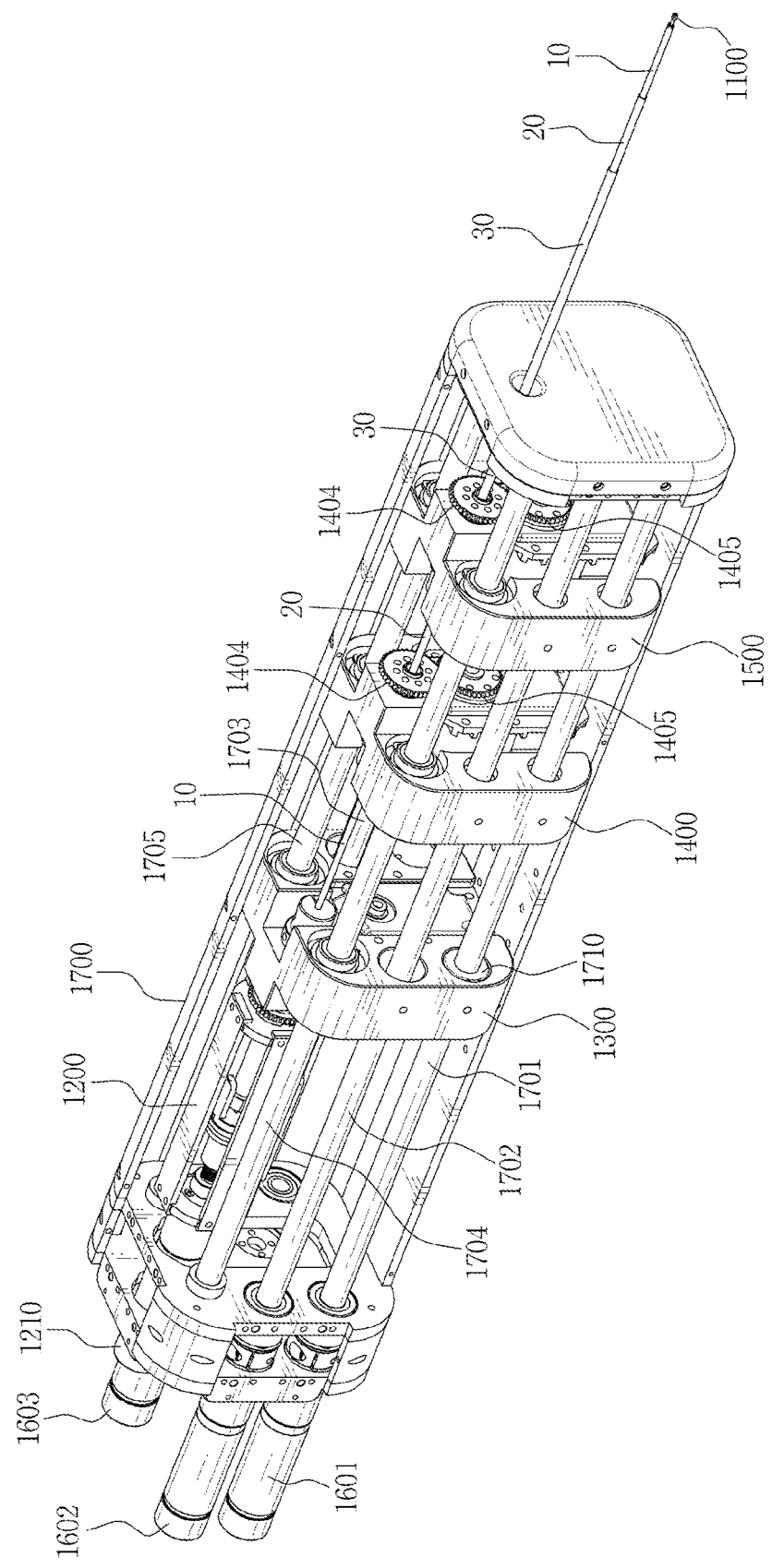
FIG. 9 illustrates an active cannular including the tube insertion device according to the embodiment.

FIG. 9 illustrates a state in which the tube insertion device according to the embodiment is applied to constitute an active cannular device.

The tube 10 illustrated in FIG. 2 is inserted into a second tube 20 having a larger diameter than the tube 10 and a different curvature from the tube 10, and the tube 20 is inserted into a third tube 30 having a larger diameter than the tube 20 and a different curvature from the tube 20.

The second tube 20 has a smaller length than the tube 10, and the third tube 30 has a smaller length than the second tube 20.

The rear end of the third tube 30 is fixed to a third fixing body 1500. The rear end of the second tube 20 is fixed to a second fixing body 1400 through the third fixing body 1500 via the rear end of the third tube 30. The rear end of the tube 10 is fixed to the fixing body 1300 through the second fixing body 1400 via the rear end of the second tube 20.

The second fixing body 1400 may rotate the second tube 20 about the longitudinal axis thereof through gears 1404 and 1405 which are rotated by a motor (not illustrated), similar to the above-described fixing body 1300.

The third fixing body 1500 may rotate the third tube 30 about the longitudinal axis thereof through gears 1504 and 1505 which are rotated by a motor (not illustrated).

According to the above-described structure, the fixing body 1300, the second fixing body 1400, and the third fixing body 1500 may rotate the tube 10, the second tube 20, and the third tube 30 independently of each other.

Furthermore, the frame 1700 has a plurality of horizontal bars 1701 to 1705 formed in the longitudinal direction thereof, and the plurality of horizontal bars 1701 to 1705 are extended through through-holes (reference numerals 1306 and 1307 of FIG. 5) formed in the fixing body 1300, the second fixing body 1400, and the third fixing body 1500.

Among the horizontal bars, two horizontal bars 1704 and 1705 at the top are used to align the fixing bodies, and the other three horizontal bars 1701, 1702, and 1703 are used to move the fixing body 1300, the second fixing body 1400, and the third fixing body 1500 forward or backward.

Referring to FIG. 9, third to fifth motors 1601 to 1603 are connected to the rear ends of the three horizontal bars 1701, 1702, and 1703, respectively, and the three horizontal bars 1701, 1702, and 1703 have a screw thread formed on the surface thereof.

A nut 1710 screwed to the screw thread of the first horizontal bar 1701 is fixed to the fixing body 1300. When the third motor 1601 is fixed, the fixing body 1300 may be moved forward or backward along the first horizontal bar 1701. On the other hand, the first horizontal bar 1701 passes through the second fixing body 1400 and the third fixing body 1500 without contact, and the second and third fixing bodies 1400 and 1500 are not moved by the rotation of the first horizontal bar 1701.

As the fixing body 1300 is moved forward or backward, the tube 10 and the tension controller 200 coupled to the fixing body 1300 are moved forward or backward.

Similarly, a nut (not illustrated) screwed to the screw thread of the second horizontal bar 1702 is fixed to the second fixing body 1400. When the fourth motor 1602 is rotated, the second fixing body 1400 may be moved forward or backward along the second horizontal bar 1702. On the other hand, the second horizontal bar 1702 passes through the fixing body 1300 and the third fixing body 1500 without contact, and the fixing body 1300 and the third fixing body 1500 are not moved by the rotation of the second horizontal bar 1702. When the second fixing body 1400 is moved forward or backward, the second tube 20 is moved forward or backward together.

Furthermore, a nut (not illustrated) screwed to the screw thread of the third horizontal bar 1703 is fixed to the third fixing body 1500. When the fifth motor 1603 is rotated, the third fixing body 1500 may be moved forward and backward along the third horizontal bar 1703. On the other hand, the third horizontal bar 1703 passes through the fixing body 1300 and the second fixing body 1400 without contact, and the fixing body 1300 and the second fixing body 1400 are not moved by the rotation of the third horizontal bar 1703. When the third fixing body 1500 is moved forward or backward, the third tube 30 is moved forward or backward together.

According to the above-described structure, the tube 10, the second tube 20, and the third tube 30 may be moved in parallel independently of each other.

Figure 10:
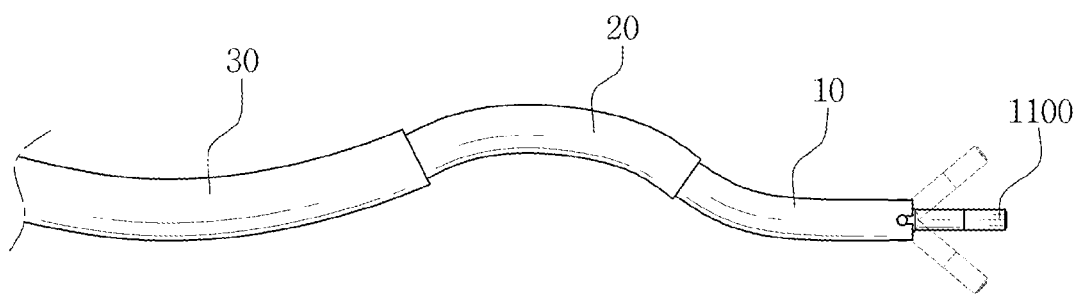
FIG. 10 illustrates a front end portion of the active cannular of FIG. 9.

As each of the tube 10, the second tube 20, and the third tube 30 is properly rotated and/or moved in parallel, the three tubes 10, 20, and 30 may be properly bent as illustrated in FIG. 10, in response to the shape of a space into which the device is inserted. Then, the end effector 1100 is located at a desired position so as to perform a proper operation through direction change.

Since the principle that the three tubes 10, 20, and 30 are properly bent in response to the shape of the space into which the device is inserted departs from the scope of the present invention, the detailed descriptions thereof are omitted herein.

Furthermore, the direction change of the end effector 1100 has been already described above.

While the present invention has been described with respect to the specific embodiments, it will be apparent to those skilled in the art that various changes and modifications may be made without departing from the spirit and scope of the invention as defined in the following claims.

What is claimed is:

1. A tube insertion device which inserts a tube into a line path to perform an operation, comprising:
   an elongated hollow tube;
   an end effector connected to a front end of the elongated hollow tube such that the direction of the end effector is changed with respect to the elongated hollow tube;
   wires connected to the end effector and extended into the elongated hollow tube;
   a tension controller controlling tensions of the wires;
   an elastic body connected to a first wire of the wires and providing a tension to the first wire through an elastic force to pull the first wire toward a rear end of the elongated hollow tube; and
   a moving body connected to a second wire of the wires, and moved to approach or separate from the elongated hollow tube, thereby controlling a tension of the second wire in the opposite direction of the tension of the first wire,
   wherein the elastic body and the moving body are disposed along an axis in which the moving body moves, and
   wherein the tension controller controls tensions of first and second wires in the opposite directions, in order to change the direction of the end effector, the wires coupled to a wire coupling portion of a spherical joint, wherein a portion of the wires run non-parallel to a longitudinal axis of the tube insertion device.

2. The tube insertion device of claim 1, further comprising a fixing body fixing the rear end of the elongated hollow tube,
   wherein the tension controller is coupled to a rear end of the fixing body, and
   the longitudinal directions of the elongated hollow tube and the tension controller are aligned with each other.

3. The tube insertion device of claim 2, wherein the elongated hollow tube and the tension controller are coupled to the fixing body so as to rotate around the longitudinal central axis of the elongated hollow tube, and the elongated hollow tube and the tension controller are simultaneously rotated by a first motor provided in the fixing body.

4. The tube insertion device of claim 3, wherein the elongated hollow tube comprises a flexible tube.

5. The tube insertion device of claim 4, wherein the elongated hollow tube comprises a micro tube made of a superelastic shape-memory alloy having a predetermined curvature.

6. The tube insertion device of claim 3, wherein the end effector is connected to the elongated hollow tube through a joint such that the direction of the end effector is changed upward and downward with respect to the elongated hollow tube, and the wires are disposed in a vertical direction so as to be connected to the end effector.

7. The tube insertion device of claim 6, wherein the end effector comprises a micro operation device which photographs, incises, cuts, penetrates, sutures, connects, welds, or lights an operation target around an insertion position inside the line path or performs an operation of applying or injecting a medicine to the operation target.

8. The tube insertion device of claim 2, wherein the elastic body comprises a coil-type spring, the second wire passes through the center of the coil-type spring, and the first and second wires are extended in parallel along the longitudinal direction of the tension controller inside the tension controller.

9. The tube insertion device of claim 2, wherein the tension controller comprises:

a frame rotatably coupled to the fixing body; and a second motor fixed to a rear end of the frame and coupled to the rear end of the moving body so as to linearly move the moving body forward or backward.

10. The tube insertion device of claim 9, wherein the frame comprises a position sensor to sense the position of the moving body.

11. The tube insertion device of claim 2, wherein the fixing body is moved forward or backward by a third motor so as to move the elongated hollow tube forward or backward.

* * * * *